United States Patent
Koverech et al.

(10) Patent No.: US 7,776,913 B2
(45) Date of Patent: Aug. 17, 2010

(54) CARNITINES FOR TREATING OR PREVENTING DISORDERS CAUSED BY ANDROPAUSE

(75) Inventors: Aleardo Koverech, Rome (IT); Giulio Biagiotti, Rome (IT); Giorgio Cavallini, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 239 days.

(21) Appl. No.: 12/076,256

(22) Filed: Mar. 14, 2008

(65) Prior Publication Data

US 2008/0287539 A1 Nov. 20, 2008

Related U.S. Application Data

(63) Continuation-in-part of application No. 10/535,509, filed as application No. PCT/IT03/00575 on Nov. 20, 2003.

(30) Foreign Application Priority Data

Dec. 13, 2002 (IT) .................. RM2002A0620

(51) Int. Cl.
*A01N 37/02* (2006.01)
*A61K 31/70* (2006.01)
*A61K 31/525* (2006.01)

(52) U.S. Cl. .................. 514/550; 514/23; 514/251
(58) Field of Classification Search .................. 514/550
See application file for complete search history.

(56) References Cited

U.S. PATENT DOCUMENTS

| 3,830,931 A | 8/1974 | De Felice |
| 4,474,812 A | 10/1984 | Cavazza |
| 5,811,457 A | 9/1998 | Corsi |
| 6,037,373 A | 3/2000 | De Simone |
| 6,063,820 A | 5/2000 | Cavazza |
| 6,090,848 A | 7/2000 | Cavazza |
| 6,245,378 B1 | 6/2001 | Cavazza |
| 6,399,116 B1 | 6/2002 | Xiu |

FOREIGN PATENT DOCUMENTS

| EP | 0 681 839 A | 11/1995 |
| EP | 0 973 415 | 1/2000 |
| WO | WO 98/43499 | 10/1998 |
| WO | WO 99/17623 | 4/1999 |
| WO | WO 03/084526 | 10/2003 |

OTHER PUBLICATIONS

G. Cavallini et al., "Oral Propionyl-L-Carnitine and Intraplaque Verapamil in the Therapy of Advanced and Resistant Reyronie's Diseare", BJU International, Blackwell Science, vol. 89, No. 9, Jun. 2002, pp. 895-900, XP001146228.
G. Biagiotti et al., "Acetyl-L-Carnitine Vs Tamoxifen in the Oral Therapy of Peyronie's Disease: A Preliminary Report", BJU International, Blackwell Science, vol. 88, No. 1, Jul. 2001, pp. 63-67, XP001106370.
iHerb.com, Carnitine, http://healthlibrary.epnet.com, copyright 1997, printed pp. 1-13, especially p. 5.

*Primary Examiner*—Sreeni Padmanabhan
*Assistant Examiner*—Timothy E Betton
(74) *Attorney, Agent, or Firm*—Lucas & Mercanti, LLP

(57) ABSTRACT

L-carnitine, propionyl L-carnitine and/or acetyl L-carnitine are used to prevent or treat disorders of male andropause caused by ageing or by chemical or surgical castration.

5 Claims, No Drawings

CARNITINES FOR TREATING OR PREVENTING DISORDERS CAUSED BY ANDROPAUSE

This application is a continuation-in-part of application Ser. No. 10/535,509 filed May 18, 2005, which in turn is the US national phase of international application PCT/IT 2003/000575 filed 20 Nov. 2003, which designated the U.S. and claims priority of IT RM 2002 A 000620, filed 13 Dec. 2002, the entire contents of each of which are hereby incorporated by reference.

The invention described herein relates to the use of acetyl L-carnitine and propionyl L-carnitine in combination for the preparation of a medicine for the prevention and/or treatment of disorders caused by the andropause.

The present invention further relates to the use of L-carnitine in combination with acetyl L-carnitine and/or propionyl L-carnitine, in a particular dosage and schedule of treatment, for the preparation of a medicine for the prevention and/or treatment of disorders caused by the andropause.

Approximately 20% of males over 50 years of age suffer from reduced libido or sexual drive and erectile function, also during the night, depression of mood, and lowering of intellectual activity, and spatial orientation capacity, as well as fatigue, irritability, reduced lean body mass, muscular capacity, mental concentration, and functioning of the hair-growing apparatus, increased visceral fat, atrophy of the skin, and reduced bone density resulting in osteopenia and osteoporosis. This syndrome has been named "androgen decline in the aging male" (ADAM) or "partial androgen deficiency of the aging male" (PADAM) or "andropause" (The Aging Male 4: 151-162, 2001).

In J. Urol. 151: 54-61, 1994 it was reported that this syndrome is due to partly modifiable age-related phenomena.

In this connection, age-related diseases are an expanding field of application owing to the rapid increase in the population aged over 60 (J. Urol. 163: 705-712, 2000).

It is claimed in several quarters that the andropause is associated with a progressive decrease in androgen production (The Aging Male 4: 151-162, 2001) and that androgen replacement therapy may be appropriately used, in the same way that oestrogen replacement therapy has been used for women in the menopause. The symptoms of andropause, in fact, are similar, though less marked, to those resulting from chemical or surgical castration for the treatment of adenocarcinoma of the prostrate: (J. Urol. 167: 2361-2368, 2002). Useful drugs for the treatment of andropause are already known. In The Aging Male 4: 151-162, 2001 it is reported that patients in the andropause obtain a fair amount of benefit if treated with 40×2 mg/day of testosterone undecaonate.

Hormone treatment for andropause is not without its drawbacks; in J. Urol. 151: 54-61, 1994, and in J. Urol. 163: 705-712, 2000, in fact, it is reported that testosterone treatment cannot be given in the presence of asymptomatic or frank prostate cancer.

In J. Impot. Res. 2002 February; 14 Suppl. 1:S93-8 it is reported that the administration of androgens may have adverse effects on the liver, on lipid status, on cardiovascular and prostate diseases, and on sleep and behavioural disorders.

Moreover, in view of the frequency of adenoma and adenocarcinoma (Rigatti P., Scattoni V.: PSA: Antigene prostatico specifico. Edizioni Medico Scientifiche (EDIMES) Pavia, 1997) it has been found that approximately 30% of patients with symptoms attributable to the andropause cannot be submitted to androgen replacement therapy.

Previous uses of propionyl L-carnitine and acetyl L-carnitine are already known.

In U.S. Pat. No. 5,811,457 the use of propionyl L-carnitine for the treatment of chronic obliterating arteriopathy is described.

In U.S. Pat. No. 6,063,820, the use of alkanoyl L-carnitines is described for the preparation of a therapeutic nutrient compound for subjects suffering from diabetes mellitus.

In European Patent EP 0 973 415, a composition is described consisting of L-carnitine, acetyl L-carnitine and propionyl L-carnitine, useful for athletes subjected to intense physical effort, or for asthenic individuals.

In patent application WO99/17623, a dietetic composition is described, consisting of L-carnitine, acetyl L-carnitine and propionyl L-carnitine for the treatment of alcohol withdrawal syndrome.

WO03084526 describes the use of L-carnitine, acety L-carnitine and propionyl L-carnitine for the preparation of a medicine for the treatment of oligoasthenoteratospermia.

In U.S. Pat. No. 6,090,848, it is reported that the combination of L-carnitine and acetyl L-carnitine is useful for the treatment of oligoasthenoteratospermia.

In the medical field there is a strongly perceived need for new therapeutic agents useful for the prevention and/or treatment of disorders of the andropause caused by ageing and by chemical or surgical castration, which do not present the drawbacks associated with the abovementioned drugs known to be useful in this field.

It has now been found that the combination of propionyl L-carnitine and acetyl L-carnitine, or one of their pharmaceutically acceptable salts proves to possess a surprising curative effect on the disorders caused by the andropause.

It is also now been found that L-carnitine in combination with acetyl L-carnitine and/or propionyl L-carnitine, in a particular dosage and schedule of treatment, is useful for the preparation of a medicine for the prevention and/or treatment of disorders caused by the andropause.

The combination according to the invention does not present the side effects of the androgens described above and can also be used in the group of patients who cannot be treated with the above-mentioned androgens.

One subject of the present invention then is the use of propionyl L-carnitine in combination with acetyl L-carnitine, or one of their pharmaceutically acceptable salts for the preparation of a medicine for the prevention and/or treatment of andropause symptoms caused by male ageing or by chemical or surgical castration, characterised by the following symptoms: reduced libido or sexual drive and erectile function, also during the night, depression of mood and lowering of intellectual activity and spatial orientation capacity, fatigue, irritability, reduced lean body mass, muscular capacity, mental concentration, and functioning of the hair-growing apparatus, increased visceral fat, atrophy of the skin, and reduced bone density resulting in osteopenia and osteoporosis.

A further object of the present invention is the use of L-carnitine in combination with acetyl L-carnitine and/or propionyl L-carnitine in which:
  L-carnitine is administered in a dose of 4 g/die for a week;
  treatment is continued for another week administering L-carnitine at a dose of 2 g/die and acetyl L-carnitine at a dose of 2 g/die;
  treatment is continued for another week administering L-carnitine at a dose of 2 g/die and propionyl L-carnitine at a dose of 1 g/die;
  treatment is continued/maintained administering L-carnitine at a dose of 2 g/die and propionyl L-carnitine at a dose of 2 g/die;

for the preparation of a medicine for the prevention and/or treatment of disorders caused by the andropause.

In the following is reported a table in which said schedule of treatment is summarized.

| | SCHEDULE OF TREATMENT | | | | |
|---|---|---|---|---|---|
| DAY | L-carnitine 4 g/day | L-carnitine 2 g/day | Acetyl L-carnitine 2 g/day | Propionyl L-carnitine 1 g/day | Propionyl L-carnitine 2 g/day |
| 1 | + | | | | |
| 2 | + | | | | |
| 3 | + | | | | |
| 4 | + | | | | |
| 5 | + | | | | |
| 6 | + | | | | |
| 7 | + | | | | |
| 8 | | + | + | | |
| 9 | | + | + | | |
| 10 | | + | + | | |
| 11 | | + | + | | |
| 12 | | + | + | | |
| 13 | | + | + | | |
| 14 | | + | + | | |
| 15 | | + | | + | |
| 16 | | + | | + | |
| 17 | | + | | + | |
| 18 | | + | | + | |
| 19 | | + | | + | |
| 20 | | + | | + | |
| 21 | | + | | + | |
| 22 | | + | | | + |
| 23 | | + | | | + |
| 24 | | + | | | + |
| 25 | | + | | | + |
| 26 | | + | | | + |
| 27 | | + | | | + |
| 28 | | + | | | + |
| 29 | | + | | | + |
| 30 | | + | | | + |
| 31 | | + | | | + |
| 1 | | + | | | + |
| 2 | | + | | | + |
| 3 | | + | | | + |

As mentioned above, the andropause is also defined as "androgen decline in the aging male" (ADAM), or "partial androgen deficiency of the aging male" (PADAM).

What is meant by a pharmaceutically acceptable salt of propionyl L-carnitine and acetyl L-carnitine is any salt of these compounds with an acid that does not give rise to unwanted toxic or side effects. Such acids are well known to pharmacologists and to experts in pharmaceutical technology.

Examples of such salts, though not exclusively these, are, for example, chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulphate, glucose phosphate, tartrate, acid tartrate, magnesium tartrate, 2-amino-ethane sulphonate, magnesium 2-amino-ethane sulphonate, choline tartrate and trichloroacetate.

L-carnitine, propionyl L-carnitine and acetyl L-carnitine can be in any form suitable for oral or parenteral administration to human subjects.

L-carnitine, propionyl L-carnitine and acetyl L-carnitine can be formulated together, as a mixture, or can be formulated separately (separate packs), using known methods. L-carnitine, propionyl L-carnitine and acetyl L-carnitine can be administered to an individual both when contained in a mixture and when packaged separately.

On the basis of various factors, such as the concentration of the active ingredients or the patient's condition, the combination according to the invention can be marketed as a health food supplement, nutritional supplement, or therapeutic product on sale with or without a compulsory prescription.

The preparation of the combination according to the present invention, when in unit dosage form, contains from 4.0 to 0.5 g of propionyl L-carnitine inner salt, and from 0.50 g to 4.0 g of acetyl L-carnitine inner salt, or an equimolar amount of one of their pharmaceutically acceptable salts.

The preferred preparation of the combination, in unit dosage form, contains 2 g of propionyl L-carnitine inner salt, and 2 g of acetyl L-carnitine inner salt, or an equimolar amount of one of their pharmaceutically acceptable salts.

It has been found, however, that, although the daily dose of the above-mentioned active ingredients to be administered depends on the patient's age, weight and condition, using professional experience, it is generally advisable to administer, in a single or in multiple doses, from approximately 0.5 to 4.0 g/day of propionyl L-carnitine, and from 4.0 to 0.5 g/day of acetyl L-carnitine, or an equimolar amount of one of their pharmaceutically acceptable salts.

Larger doses can be administered thanks to the extremely low toxicity of said active ingredients.

Reported here below is a clinical trial conducted in order to evaluate the activity of the combination according to the association in the treatment of the symptoms of male ageing.

The determinations carried out during the clinical trial were aimed at assessing any pathological changes affecting the cervico-urethral district and the efficacy of the compound according to the invention as compared to the comparator compound.

The patients recruited into the trial had to match up to the following inclusion/exclusion criteria.

Inclusion Criteria

Patients aged over 60 years with lowered blood concentrations of free and total testosterone (The Aging Male 4: 151-162, 2001) and complaining of symptoms figuring in the working definition of andropause proposed by the International Society for the Study of the Aging Male (I.S.S.A.M.) (The Aging Male 4: 151-162, 2001): reduced libido or sex drive and erectile function, depressed mood, difficulty concentrating, irritability and fatigue.

Exclusion Criteria

Obstruction or inflammation of the lower urinary tract; prostate volume>20 $cm^3$ at suprapubic ultrasonography; increased concentration of prostate-specific antigen (PSA); increased suspicion regarding prostate consistency at rectal exploration (Am. J. Med. 110: 563-571, 2001); heavy smokers and drinkers; recent myocardial infarct (<6 months); diabetes; hypertension or other untreated cardiovascular diseases; active cancer; use of psychotropic drugs or anticancer therapy; recent major surgery (<6 months); increased prolactinaemia.

In all, 73 patients were included, 13 of whom failed to complete the trial.

The results obtained, reported here below, refer to 60 patients with a mean age of 66 years (range: 60-74).

The patients were divided at random into 4 groups of 15 each and treated as reported in the following:
(1) First group received (was treated with) testosterone undecaonate (Andriol[R]-Organon) 40×2 mg/day;
(2) Second group received propionyl L-carnitine 1+1 g/day associated with acetyl L-carnitine 1+1 g/day;

(3) Third group was treated orally according to the following schedule of treatment:
   days 1-7: L-carnitine in a dose of 4 g/day;
   days 8-14: L-carnitine in a dose of 2 g/day and acetyl L-carnitine at a dose of 2 g/die;
   days 15-21: L-carnitine in a dose of 2 g/day and propionyl L-carnitine at a dose of 1 g/die;
   said treatment was continued/maintained administering L-carnitine at a dose of 2 g/die and propionyl L-carnitine at a dose of 2 g/die;
(4) fourth group received vitamin C (Redoxon$^R$-Roche) 500 mg/day as a placebo.

The above-mentioned compounds were presented to the patients in anonymous containers and administered for 6 months.

Data Collection

Medical history-taking and physical examinations were done for all patients. The following data were also collected prior to the start of treatment, after 1, 3 and 6 months of treatment:
1. Total blood prostate-specific antigen (PSA) (ng/ml) as measured with the automatic test and monoclonal antibodies [Rigatti P., Scattoni V.: PSA: Antigene prostatico specifico. Edizioni Medico Scientifiche (EDIMES) Pavia, 1997].
2. Prostate volume (cm$^3$) as measured by suprapubic ultrasonography and calculated by means of the three diameters rule [Rigatti P. Scattoni V.: PSA: Antigene prostatico specifico. Edizioni Medico Scientifiche (EDIMES) Pavia, 1997].
3. Peak systolic volume (PSV) (cm/sec), end-diastolic velocity (EDV) (cm/sec), and Resistance Index (RI) (%) of the penile arteries (right and left cavernous e dorsal) as measured by means of penile basal and dynamic colour Doppler ultrasonography. RI was calculated as follows: (PSV-EDV/EDV)×100 (Urology 1997: 49: 822-830).
4. Duration of full erections (in minutes) in the course of a recording period of three nights performed with Rigiscan. What is meant by full erection is an increase in rigidity greater than 70% above the basal line and an increase in diameter>2 cm at the head and >3 cm at the base (Eardly I, Sethia K.: Erectile dysfunction Current Management and Treatment. The Mosby Company, London 1998).
5. Free and total blood testosterone, LH and prolactin levels (The Aging Male 4: 151-162, 2001).
6. Sexual function was checked by means of semistructured interviews and administration of the International Index of Erectile Function (IIEF-15) (Urology 1997: 49: 822-830). A score was calculated for each patient.
7. Depression was quantified by means of the Hamilton Depression Scale questionnaire (DMS III) (Cancer 94: 2481-2489, 2002). A score was calculated for each patient.
8. The subjective sensation of fatigue was calculated using the fatigue scale (Lison L.: Statistica applicata alla biologia sperimentale. Milano: Casa Editrice Ambrosiana, 1972). A score was calculated for each patient.
9. Side effects.

Blood concentrations of PSA, free and total testosterone, prolactin LH, prostate volume, PSV, EDV, RI, full erection duration, IIEF-15, DMS III, and fatigue scale scores were compared between and within groups by means of factorial analysis of variance for randomised blocks (1 patient=1 block). Comparison of the mean values was done on the raw data with the exclusion of RI which used data subjected to angular transformation ($\sin^{-1} \sqrt{P/100}$) for the comparisons. Side effects were compared using the chi-square etst (Lison L.: Statistica applicata alla biologia sperimentale. Milano: Casa Editrice Ambrosiana, 1972).

The results obtained are given in the following examples.

EXAMPLE 1

Table 1 shows the mean PSA levels in the four patient groups before, during and after therapy with the combination according to the invention, with the comparator compound (testosterone) and with a placebo.

The results obtained, presented in Table 1, show that the treatment with the compounds tested induced no significant changes.

TABLE 1

| Group | Type of therapy | Observation time | PSA ng/ml |
|---|---|---|---|
| 1 | Testosterone undecaonate 40 × 2 mg/day | Before therapy | 2.02 ± 0.74 |
|   |   | 3 months | 2.01 ± 0.79 |
|   |   | 6 months | 2.02 ± 0.85 |
| 2 | Propionyl L-carnitine 1 × 2 g/day + acetyl L-carnitine 1 × 2 g/day | Before therapy | 2.36 ± 0.87 |
|   |   | 3 months | 2.21 ± 0.654 |
|   |   | 6 months | 2.33 ± 0.77 |
| 3 | Schedule of treatment L-carnitine + acetyl L-carnitine + propionyl L-carnitine | Before therapy | 1.80 ± 0.77 |
|   |   | 1 month | 1.75 ± 0.80 |
|   |   | 3 months | 1.77 ± 0.95 |
| 4 | Placebo | Before therapy | 1.80 ± 0.77 |
|   |   | 3 months | 1.75 ± 0.75 |
|   |   | 6 months | 1.75 ± 0.75 |

Mean serum levels of total prostate-specific antigen (PSA) ng/ml before, during and after administration of: Group 1: testosterone undecaonate (40 × 2 mg/day), for 6 months; Group 2: propionyl L-carnitine 1 × 2 g/ day + acetyl L-carnitine 1 × 2 g/day, for 6 months; Group 3: schedule of treatment (days 1-7: L-carnitine in a dose of 4 g/day; days 8-14: L-carnitine in a dose of 2 g/day and acetyl L-carnitine at a dose of 2 g/die; days 15-21: L-carnitine in a dose of 2 g/day and propionyl L-carnitine at a dose of 1 g/die; treatment continued/maintained with L-carnitine at a dose of 2 g/die and propionyl L-carnitine at a dose of 2 g/die), for 3 months; or Group 4: placebo, for 6 months; to the groups of 15 patients each. Data are mean ± standard deviation.

These results indicate that the treatment with testosterone, with the combination according to the invention and with placebo did not significantly increase blood PSA levels.

EXAMPLE 2

Table 2 presents the data for mean prostate volume values before, during and after therapy with testosterone, with the combination according to the invention and with placebo.

TABLE 2

Mean prostate volume (cm$^3$) as measured by suprapubic ultrasonography and calculation of the three diameters.

| Group | Type of therapy | Observation time | Prostate volume (cm$^3$) |
|---|---|---|---|
| 1 | Testosterone undecaonate 40 × 2 mg/day | Before therapy | 15.3 ± 2.8 |
|   |   | 3 months | 15.5 ± 3.0 |
|   |   | After therapy (6 mos) | 15.5 ± 2.6 |
| 2 | Propionyl L-carnitine 1 × 2 g/day + acetyl L-carnitine 1 × 2 g/day | Before therapy | 15.2 ± 2.7 |
|   |   | 3 months | 14.5 ± 2.6 |
|   |   | 6 months | 15.1 ± 3.1 |
| 3 | Schedule of treatment L-carnitine + acetyl L-carnitine + propionyl L-carnitine | Before therapy | 14.7 ± 3.6 |
|   |   | 1 month | 14.9 ± 2.4 |
|   |   | 3 months | 14.7 ± 3.0 |
| 4 | Placebo | Before therapy | 15.6 ± 3.2 |
|   |   | 3 months | 15.5 ± 3.4 |
|   |   | 6 months | 15.6 ± 3.3 |

Data are mean ± standard deviation.

The results presented in Table 2 indicate that the treatment with the compounds tested did not significantly increase prostate volume.

EXAMPLES 3 AND 4

Table 3 presents the data for peak systolic velocity (PSV) of the right cavernous artery of the penis before, during and after therapy with the combination according to the invention, with testosterone and with placebo.

TABLE 3

Peak systolic velocity (PSV) (mean value in cm/sec) of the right cavernous artery of the penis as measured by dynamic colour Doppler ultrasonography.

| Group | Type of therapy | Observation time | Right cavernous artery PSV (cm/sec) |
|---|---|---|---|
| 1 | Testosterone undecaonate 40 × 2 mg/day | Before therapy<br>3 months<br>6 months | 33.2 ± 3.9<br>32.8 ± 4.2<br>33.7 ± 3.7 |
| 2 | Propionyl L-carnitine 1 × 2 g/day + acetyl L-carnitine 1 × 2 g/day | Before therapy<br>3 months<br>6 months | 33.9 ± 3.2<br>33.9 ± 3.2<br>33.9 ± 3.3 |
| 3 | Schedule of treatment L-carnitine + acetyl L-carnitine + propionyl L-carnitine | Before therapy<br>1 month<br>3 months | 28.7 ± 2.7<br>39.2 ± 2.6<br>40.0 ± 3.0 |
| 4 | Placebo | Before therapy<br>3 months<br>6 months | 33.7 ± 4.3<br>33.9 ± 5.0<br>33.8 ± 4.7 |

Data are mean ± standard deviation.

TABLE 4

Peak systolic velocity (PSV) (mean value in cm/sec) of the left cavernous artery of the penis as measured by dynamic colour Doppler ultrasonography.

| Group | Type of therapy | Observation time | Left cavernous PSV (cm/sec) |
|---|---|---|---|
| 1 | Testosterone undecaonate 40 × 2 mg/day | Before therapy<br>3 months<br>6 months | 33.6 ± 3.7<br>32.6 ± 4.2<br>33.5 ± 3.5 |
| 2 | Propionyl L-carnitine 1 × 2 g/day + acetyl L-carnitine 1 × 2 g/day | Before therapy<br>3 months<br>6 months | 34.1 ± 3.3<br>34.2 ± 3.3<br>34.1 ± 3.5 |
| 3 | Schedule of treatment L-carnitine + acetyl L-carnitine + propionyl L-carnitine | Before therapy<br>1 month<br>3 months | 29.6 ± 3.6<br>38.6 ± 4.0<br>39.6 ± 4.1 |
| 4 | Placebo | Before therapy<br>3 months<br>6 months | 33.4 ± 4.0<br>32.5 ± 4.8<br>32.7 ± 4.9 |

Data are mean ± standard deviation.

The results presented in Tables 3 and 4 indicate that the treatment with the compounds tested did not induce significant changes.

Only the group treated with the schedule of treatment shows a result statistically significant ($p<0.01$) both after 1 and 3 months of treatment.

EXAMPLES 5, 6, 7 AND 8

The results presented in Tables 5, 6, 7 and 8 here below show that the treatments administered also induced no significant differences either in the case of the other vascular parameters (EDV and RI) or as affecting the right or left cavernous arteries.

Only the group treated with the schedule of treatment shows results significant both after 1 and 3 months of treatment.

TABLE 5

End-diastolic velocity (EDV) (mean value in cm/sec) of the right cavernous artery of the penis as measured by dynamic colour Doppler ultrasonography.

| Group | Type of therapy | Observation time | Right cavernous artery EDV (cm/sec) |
|---|---|---|---|
| 1 | Testosterone undecaonate 40 × 2 mg/day | Before therapy<br>3 months<br>6 months | 7.8 ± 3.6<br>7.9 ± 3.6<br>7.9 ± 3.6 |
| 2 | Propionyl L-carnitine 1 × 2 g/day + acetyl L-carnitine 1 × 2 g/day | Before therapy<br>3 months<br>6 months | 6.8 ± 3.6<br>7.1 ± 3.8<br>6.9 ± 3.6 |
| 3 | Schedule of treatment L-carnitine + acetyl L-carnitine + propionyl L-carnitine | Before therapy<br>1 month<br>3 months | 7.9 ± 3.4<br>4.2 ± 1.2<br>4.1 ± 1.1 |
| 4 | Placebo | Before therapy<br>3 months<br>6 months | 6.5 ± 3.8<br>6.7 ± 4.0<br>6.7 ± 4.3 |

Data are mean ± standard deviation.

TABLE 6

End-diastolic velocity (EDV) (mean value in cm/sec) of the left cavernous artery of the penis as measured by dynamic colour Doppler ultrasonography.

| Group | Type of therapy | Observation time | Left cavernous artery EDV (cm/sec) |
|---|---|---|---|
| 1 | Testosterone undecaonate 40 × 2 mg/day | Before therapy<br>3 months<br>6 months | 7.7 ± 3.5<br>7.5 ± 3.3<br>7.4 ± 3.3 |
| 2 | Propionyl L-carnitine 1 × 2 g/day + acetyl L-carnitine 1 × 2 g/day | Before therapy<br>3 months<br>6 months | 6.4 ± 3.6<br>6.4 ± 3.3<br>6.5 ± 3.2 |
| 3 | Schedule of treatment L-carnitine + acetyl L-carnitine + propionyl L-carnitine | Before therapy<br>1 month<br>3 months | 7.7 ± 3.1<br>4.4 ± 1.4<br>4.5 ± 1.8 |
| 4 | Placebo | Before therapy<br>3 months<br>6 months | 6.9 ± 3.8<br>6.3 ± 3.8<br>6.2 ± 3.8 |

Data are mean ± standard deviation.

TABLE 7

Resistance Index (RI) (%) of right cavernous artery.

| Group | Type of therapy | Observation time | Right cavernous artery RI % |
|---|---|---|---|
| 1 | Testosterone undecaonate 40 × 2 mg/day | Before therapy<br>3 months<br>6 months | 64.6 ± 8.4<br>60.9 ± 8.4<br>61.1 ± 7.9 |

TABLE 7-continued

Resistance Index (RI) (%) of right cavernous artery.

| Group | Type of therapy | Observation time | Right cavernous artery RI % |
|---|---|---|---|
| 2 | Propionyl L-carnitine 1 × 2 g/day + acetyl L-carnitine 1 × 2 g/day | Before therapy 3 months 6 months | 64.2 ± 7.4 63.7 ± 7.4 64.1 ± 7.3 |
| 3 | Schedule of treatment L-carnitine + acetyl L-carnitine + propionyl L-carnitine | Before therapy 1 month 3 months | 59.8 ± 8.8 66.4 ± 7.2 68.7 ± 8.9 |
| 4 | Placebo | Before therapy 3 months 6 months | 64.5 ± 8.8 64.4 ± 9.2 64.7 ± 9.9 |

Data used were values subjected to angular transformation ($\sin^{-1}\sqrt{P/100}$) and presented as mean ± standard deviation.

TABLE 8

Resistance Index (RI) (%) of left cavernous artery.

| Group | Type of therapy | Observation time | Left cavernous artery RI % |
|---|---|---|---|
| 1 | Testosterone undecaonate 40 × 2 mg/day | Before therapy 3 months 6 months | 61.5 ± 8.3 61.5 ± 7.8 62.1 ± 7.0 |
| 2 | Propionyl L-carnitine 1 × 2 g/day + acetyl L-carnitine 1 × 2 g/day | Before therapy 3 months 6 months | 64.8 ± 6.8 64.9 ± 7.0 64.7 ± 7.0 |
| 3 | Schedule of treatment L-carnitine + acetyl L-carnitine + propionyl L-carnitine | Before therapy 1 month 3 months | 60.2 ± 7.4 67.4 ± 7.6 69.2 ± 8.2 |
| 4 | Placebo | Before therapy 3 months 6 months | 63.3 ± 8.7 64.6 ± 9.6 64.7 ± 8.7 |

Data used were values submitted to angular transformation ($\sin^{-1}\sqrt{P/100}$) and presented as means ± standard deviation.

EXAMPLE 9

Table 9 presents the data for duration of full nocturnal erections in minutes recorded by Rigiscan for a period of 3 nights before, during and after therapy with the combination according to the invention, with testosterone and with placebo. The combination according to the invention induced a significant increase in duration of full nocturnal erections both at 3 (F=11.6; P<0.01) and at 6 months (F =19.1; P<0.01), while the administration of testosterone induced a significant increase in duration of full nocturnal erections at 6 months (F=12.4, P<0.01), but not at 3 months (F=1.01; P=n.s.). In addition, the duration of the nocturnal erections was greater after 6 months in the group treated with the combination according to the invention (F=4.2, P<0.05) than that of those observed after 6 months in the group treated with testosterone. The administration of placebo had no effect on the duration of full nocturnal erections (F=2.4, P=n.s.).

TABLE 9

Duration of full erections (in minutes) in the course of a recording period of three nights by Rigiscan.

| Group | Type of therapy | Observation time | Duration of full erections (in minutes) |
|---|---|---|---|
| 1 | Testosterone undecaonate 40 × 2 mg/day | Before therapy 3 months 6 months | 108.3 ± 18.7 112.7 ± 21.1 119.6 ± 26.0 |
| 2 | Propionyl L-carnitine 1 × 2 g/day + acetyl L-carnitine 1 × 2 g/day | Before therapy 3 months 6 months | 98.9 ± 18.5 112.8 ± 16.1 136.9 ± 28.1 |
| 3 | Schedule of treatment L-carnitine + acetyl L-carnitine + propionyl L-carnitine | Before therapy 1 month 3 months | 96.3 ± 17.4 125.7 ± 19.5 138.9 ± 20.5 |
| 4 | Placebo | Before therapy 3 months 6 months | 105.3 ± 21.2 107.7 ± 21.2 102.6 ± 22.9 |

Data are mean ± standard deviation.

These results indicate that the compounds of the invention are significantly more active than testosterone in increasing nocturnal erections (by means of a non-psychological and non-macrovascular organic mechanism).

The best results were obtained using the schedule of treatment according to the present invention (p<0.01).

EXAMPLES 10 AND 11

Table 10 presents the data for blood total testosterone levels before, during and after therapy with the combination according to the invention, with testosterone and with placebo. The treatment with the compounds tested induced no significant changes.

In particular, administration of the combination according to the invention, of testosterone and of placebo induced no significant increases in total serum testosterone at either 3 or 6 months.

TABLE 10

Blood levels of total testosterone.

| Group | Type of therapy | Observation time | Total testosterone nmol/l |
|---|---|---|---|
| 1 | Testosterone undecaonate 40 × 2 mg/day | Before therapy 3 months 6 months | 14.5 ± 2.1 15.5 ± 3.9 15.8 ± 2.6 |
| 2 | Propionyl L-carnitine 1 × 2 g/day + acetyl L-carnitine 1 × 2 g/day | Before therapy 3 months 6 months | 15.9 ± 2.8 15.2 ± 3.0 15.8 ± 4.4 |
| 3 | Schedule of treatment L-carnitine + acetyl L-carnitine + propionyl L-carnitine | Before therapy 1 month 3 months | 14.7 ± 2.2 13.9 ± 2.5 14.7 ± 2.3 |
| 4 | Placebo | Before therapy 3 months 6 months | 14.9 ± 2.0 14.8 ± 2.3 14.9 ± 1.9 |

Data are mean ± standard deviation.

These results indicate that the activity of oral testosterone is exerted mainly through an increase in free and total blood testosterone, whereas the compound according to the invention acts in a different way, probably through restoration of the physiological concentration of ROS.

Very similar results were obtained on analysing free blood testosterone during treatment with the compounds tested. The results obtained are presented in Table 11.

TABLE 11

Blood levels of free testosterone.

| Group | Type of therapy | Observation time | Free blood testosterone pg/ml |
|---|---|---|---|
| 1 | Testosterone undecaonate 40 × 2 mg/day | Before therapy 3 months 6 months | 4.4 ± 0.8 19.5 ± 4.2 19.7 ± 4.0 |
| 2 | Propionyl L-carnitine 1 × 2 g/day + acetyl L-carnitine 1 × 2 g/day | Before therapy 3 months 6 months | 4.6 ± 1.0 4.5 ± 1.1 4.5 ± 0.8 |
| 3 | Schedule of treatment L-carnitine + acetyl L-carnitine + propionyl L-carnitine | Before therapy 1 month 3 months | 4.6 ± 1.2 4.6 ± 0.9 4.3 ± 1.5 |
| 4 | Placebo | Before therapy 3 months 6 months | 4.2 ± 0.6 4.3 ± 0.8 4.1 ± 0.7 |

Data are mean ± standard deviation.

EXAMPLE 12

Table 12 presents the data for blood levels of LH before, during and after treatment with the combination according to the invention, with testosterone and with placebo.

In particular, treatment with the combination according to the invention and with placebo induced no significant changes in LH either at 3 or at 6 months ($F<1$, $P=n.s.$). In contrast, the administration of testosterone led to a statistically significant reduction in blood levels of LH at 3 months ($F=229$ $P<0.01$), and a significant reduction at 6 months.

TABLE 12

Blood levels of LH.

| Group | Type of therapy | Observation time | LH IU/l |
|---|---|---|---|
| 1 | Testosterone undecaonate 40 × 2 mg/day | Before therapy 3 months 6 months | 8.9 ± 0.6 4.3 ± 0.6 4.2 ± 1.2 |
| 2 | Propionyl L-carnitine 1 × 2 g/day + acetyl L-carnitine 1 × 2 g/day | Before therapy 3 months 6 months | 8.4 ± 0.9 8.5 ± 0.7 8.5 ± 0.8 |
| 3 | Schedule of treatment L-carnitine + acetyl L-carnitine + propionyl L-carnitine | Before therapy 1 month 3 months | 8.3 ± 0.7 8.2 ± 0.9 8.6 ± 1.1 |
| 4 | Placebo | Before therapy 3 months 6 months | 8.7 ± 0.6 8.6 ± 0.6 8.7 ± 0.5 |

Data are mean ± standard deviation.

These results confirm that it is the rise in free blood testosterone that causes the activity of testosterone in resolving the symptoms associated with ageing.

EXAMPLE 13

Table 13 presents the data for blood prolactin levels before, during and after treatment with the combination according to the invention, with testosterone and with placebo. The results obtained show that the treatment did not induce any significant changes.

TABLE 13

Blood prolactin levels.

| Group | Type of therapy | Observation time | Prolactin mcg/ml |
|---|---|---|---|
| 1 | Testosterone undecaonate 40 × 2 mg/day | Before therapy 3 months 6 months | 7.7 ± 1.6 7.4 ± 1.7 7.3 ± 1.8 |
| 2 | Propionyl L-carnitine 1 × 2 g/day + acetyl L-carnitine 1 × 2 g/day | Before therapy 3 months 6 months | 7.6 ± 1.9 7.4 ± 1.9 7.5 ± 2.2 |
| 3 | Schedule of treatment L-carnitine + acetyl L-carnitine + propionyl L-carnitine | Before therapy 1 month 3 months | 7.6 ± 1.6 7.8 ± 1.9 7.7 ± 1.7 |
| 4 | Placebo | Before therapy 3 months 6 months | 7.4 ± 1.7 7.7 ± 1.7 7.3 ± 1.8 |

Data are mean ± standard deviation.

These results indicate that oral testosterone and the combination according to the invention are capable of increasing libido regardless of prolactin (a hormone an increase in which gives rise to a reduction of libido and vice versa).

EXAMPLE 14

Table 14 presents the scores on the International Index of Erectile Function questionnaire (IIEF-15)—"Erectile Function" section, before, during and after therapy with the compounds of the invention, with testosterone and with placebo.

Testosterone induced a significant increase in scores both at 3 months $F=6.3$, $P<0.05$; and 6 months $F=29.2$, $P<0.01$.

The combination according to the invention (Group 2) induced a significant increase in scores both at 3 months $F=31.5$, $P<0.01$; and 6 months $F=18.9$, $P<0.01$.

The schedule of treatment according to the invention (Group 3) induced a significant increase in scores both at 1 months $F=25.5$, $P<0.01$; and 3 months $F=31.5$, $P<0.01$.

Administration of the placebo induced no significant changes in scores.

TABLE 14

Scores on the International Index of Erectile Function questionnaire (IIEF-15) - "Erectile Function" section.

| Group | Type of therapy | Observation time | Score |
|---|---|---|---|
| 1 | Testosterone undecaonate 40 × 2 mg/day | Before therapy 3 months 6 months | 13.8 ± 2.7 16.7 ± 3.7 20.2 ± 5.3 |
| 2 | Propionyl L-carnitine 1 × 2 g/day + acetyl L-carnitine 1 × 2 g/day | Before therapy 3 months 6 months | 11.4 ± 5.4 16.7 ± 5.4 21.9 ± 7.3 |
| 3 | Schedule of treatment L-carnitine + acetyl L-carnitine + propionyl L-carnitine | Before therapy 1 month 3 months | 13.6 ± 1.4 23.9 ± 1.4 24.5 ± 2.9 |
| 4 | Placebo | Before therapy 3 months 6 months | 13.8 ± 1.1 12.9 ± 2.0 14.2 ± 2.9 |

Data are mean ± standard deviation.

These results indicate that the compounds of the invention and oral testosterone significantly increase erectile activity, whereas the placebo proves inactive.

EXAMPLES 15 AND 16

Very similar results were obtained in the "Intercourse Satisfaction" (Table 15) and "Sexual Desire" sections (Table 16).
These results too indicate the compounds of the invention and oral testosterone significantly increased intercourse satisfaction and sexual desire.

TABLE 15

Scores on the International Index of Erectile Function questionnaire (IIEF-15) - "Intercourse Satisfaction" section.

| Group | Type of therapy | Observation time | Score |
|---|---|---|---|
| 1 | Testosterone undecaonate 40 × 2 mg/day | Before therapy 3 months 6 months | 4.1 ± 0.8 4.8 ± 0.8 5.8 ± 1.9 |
| 2 | Propionyl L-carnitine 1 × 2 g/day + acetyl L-carnitine 1 × 2 g/day | Before therapy 3 months 6 months | 4.6 ± 1.0 5.3 ± 1.2 6.9 ± 2.5 |
| 3 | Schedule of treatment L-carnitine + acetyl L-carnitine + propionyl L-carnitine | Before therapy 1 month 3 months | 4.3 ± 0.9 6.8 ± 0.7 7.2 ± 0.9 |
| 4 | Placebo | Before therapy 3 months 6 months | 3.9 ± 0.8 4.3 ± 0.8 4.1 ± 0.7 |

Data are mean ± standard deviation.

TABLE 16

Scores on the International Index of Erectile Function questionnaire (IIEF-15) - "Sexual Desire" section.

| Group | Type of therapy | Observation time | Score |
|---|---|---|---|
| 1 | Testosterone undecaonate 40 × 2 mg/day | Before therapy 3 months 6 months | 4.3 ± 1.0 5.7 ± 0.8 7.1 ± 0.9 |
| 2 | Propionyl L-carnitine 1 × 2 g/day + acetyl L-carnitine 1 × 2 g/day | Before therapy 3 months 6 months | 3.9 ± 0.8 6.6 ± 1.3 7.3 ± 1.9 |
| 3 | Schedule of treatment L-carnitine + acetyl L-carnitine + propionyl L-carnitine | Before therapy 1 month 3 months | 3.4 ± 1.1 5.9 ± 1.2 7.5 ± 1.3 |
| 4 | Placebo | Before therapy 3 months 6 months | 3.3 ± 0.9 3.3 ± 0.9 3.5 ± 0.5 |

Data are means ± standard deviation.

EXAMPLE 17

Table 17 presents the scores on the International Index of Erectile Function questionnaire (IIEF-15)—"General Satisfaction" section, before, during and after therapy with the compounds of the invention, testosterone or placebo.
The treatment induced significant changes; in particular:
the combination of the invention (Group 2) significantly increased the scores at 3 months (F=33.3 P<0.01) and at 6 months (F=33.6, P<0.01).
the schedule of treatment of the invention (Group 3) significantly increased the scores at 1 months (F=33.6 P<0.01) and at 3 months (F=33.9, P<0.01).
The administration of testosterone and placebo failed to induce any significant changes in scores.

TABLE 17

Scores on the International Index of Erectile Function questionnaire (IIEF-15) - "Orgasmic Function" section.

| Group | Type of therapy | Observation time | Score |
|---|---|---|---|
| 1 | Testosterone undecaonate 40 × 2 mg/day | Before therapy 3 months 6 months | 3.2 ± 1.2 3.9 ± 0.9 4.7 ± 1.8 |
| 2 | Propionyl L-carnitine 1 × 2 g/day + acetyl L-carnitine 1 × 2 g/day | Before therapy 3 months 6 months | 3.7 ± 1.1 5.4 ± 1.3 7.2 ± 1.1 |
| 3 | Schedule of treatment L-carnitine + acetyl L-carnitine + propionyl L-carnitine | Before therapy 1 month 3 months | 3.0 ± 0.8 7.0 ± 1.1 7.5 ± 1.3 |
| 4 | Placebo | Before therapy 3 months 6 months | 2.9 ± 0.7 3.4 ± 1.6 3.0 ± 0.6 |

Data are mean ± standard deviation.

These results indicate that the combination according to the invention are significantly more active than testosterone and placebo in increasing the general well-being (coenaesthesia) of patients receiving the therapy.

EXAMPLE 18

Table 18 presents the scores on the International Index of Erectile Function questionnaire (IIEF-15)—"Orgasmic Function" section, before, during and after therapy with the compounds of the invention, with testosterone and with placebo.

The combination according to the invention significantly increased the scores at 3 months (F=33.6, P<0.01) and 6 months (F=21, P<0.01).

The schedule of treatment of the invention (Group 3) significantly increased the scores at 1 months (F=33.7 P<0.01) and at 3 months (F=33.9, P<0.01).

The administration of testosterone significantly increased the scores at 3 months (F=12.6, P<0.01) but not at 6 months (F=2.3, P=n.s.).

Placebo did not induce any significant changes in score.

TABLE 18

Scores on the International Index of Erectile Function questionnaire (IIEF-15) - "General Satisfaction" section.

| Group | Type of therapy | Observation time | Score |
|---|---|---|---|
| 1 | Testosterone undecaonate 40 × 2 mg/day | Before therapy 3 months 6 months | 3.2 ± 0.6 3.7 ± 1.1 4.4 ± 2.2 |
| 2 | Propionyl L-carnitine 1 × 2 g/day + acetyl L-carnitine 1 × 2 g/day | Before therapy 3 months 6 months | 3.1 ± 0.6 5.2 ± 1.5 7.1 ± 1.8 |
| 3 | Schedule of treatment L-carnitine + acetyl L-carnitine + propionyl L-carnitine | Before therapy 1 month 3 months | 3.0 ± 0.8 6.4 ± 0.6 6.9 ± 1.2 |
| 4 | Placebo | Before therapy 3 months 6 months | 2.8 ± 0.7 2.9 ± 0.5 3.1 ± 0.8 |

Data are mean ± standard deviation.

These results indicate the compounds of the invention proved significantly more active than testosterone.

EXAMPLE 19

Table 19 presents the scores on the DMS III questionnaire before, during and after therapy with the combination according to the invention, with testosterone and with placebo.

The combination of the invention (Group 2) induced a significant decrease in DMS III scores both at 3 months ($F=19.2$; $P<0.01$) and at 6 months ($F=13.0$; $P<0.01$).

The schedule of treatment of the invention (Group 3) induced a significant decrease in DMS III scores both at 1 months ($F=19.1$; $P<0.01$) and at 3 months ($F=12.8$; $P<0.01$).

The administration of testosterone induced a significant decrease in DMS III scores at 3 months ($F=4.07$; $P<0.05$), but not at 6 months ($F=2.5$; $P=n.s.$). The administration of placebo induced a significant decrease in DMS III scores at 3 months ($F=7.75$; $P<0.05$), but not at 6 months ($F=1$; $P=n.s.$).

No significant difference was detected between the scores obtained at 6 months with placebo and testosterone ($F<1$, $P=n.s.$), whereas the score obtained with the compounds of the invention was significantly lower.

TABLE 19

Scores on the Hamilton Depression Scale questionnaire (DMS III).

| Group | Type of therapy | Observation time | Score |
|---|---|---|---|
| 1 | Testosterone undecaonate 40 × 2 mg/day | Before therapy<br>3 months<br>6 months | 6.6 ± 1.0<br>5.8 ± 0.7<br>5.1 ± 1.3 |
| 2 | Propionyl L-carnitine 1 × 2 g/day + acetyl L-carnitine 1 × 2 g/day | Before therapy<br>3 months<br>6 months | 6.3 ± 1.1<br>4.7 ± 0.9<br>3.2 ± 1.1 |
| 3 | Schedule of treatment L-carnitine + acetyl L-carnitine + propionyl L-carnitine | Before therapy<br>1 month<br>3 months | 6.9 ± 0.7<br>3.4 ± 0.9<br>3.1 ± 1.2 |
| 4 | Placebo | Before therapy<br>3 months<br>6 months | 6.8 ± 0.8<br>5.8 ± 0.7<br>5.5 ± 1.1 |

Data are mean ± standard deviation.

These results indicate that the compounds of the invention are significantly more active than testosterone and placebo (which exhibit similar activity) in improving the mood of subjects receiving the treatment.

EXAMPLE 20

Table 20 presents the scores on the fatigue scale questionnaire before, during and after therapy with the compounds of the invention, with testosterone and with placebo.

The combination according to the invention (Group 1) induced a statistically significant increase in the scores at 3 months ($F=12.2$, $P<0.01$) and at 6 months ($F=9.3$, $P<0.01$).

The schedule of treatment of the invention (Group 3) induced a significant increase in the scores both at 1 months ($F=12.1$; $P<0.01$) and at 3 months ($F=9.1$; $P<0.01$).

The administration of testosterone induced a statistically significant increase in the score at 3 months ($F=33.6$, $P<0.01$) but no significant increase at 6 months ($F=5.9$, $P=n.s.$).

Placebo induced no significant changes in score.

TABLE 20

Scores on the fatigue scale.

| Group | Type of therapy | Observation time | Score |
|---|---|---|---|
| 1 | Testosterone undecaonate 40 × 2 mg/day | Before therapy<br>3 months<br>6 months | 2.8 ± 1.3<br>1.1 ± 1.0<br>0.6 ± 0.4 |
| 2 | Propionyl L-carnitine 1 × 2 g/day + acetyl L-carnitine 1 × 2 g/day | Before therapy<br>3 months<br>6 months | 2.7 ± 1.3<br>1.3 ± 1.1<br>0.5 ± 0.4 |
| 3 | Schedule of treatment L-carnitine + acetyl L-carnitine + propionyl L-carnitine | Before therapy<br>1 month<br>3 months | 3.0 ± 0.0<br>0.5 ± 0.4<br>0.4 ± 0.4 |
| 4 | Placebo | Before therapy<br>3 months<br>6 months | 2.9 ± 0.8<br>2.9 ± 0.8<br>3.0 ± 0.8 |

Data are mean ± standard deviation.

The results presented in Table 20 indicate that testosterone and the compounds of the invention are significantly more active than placebo in increasing the sensation of general well-being in the patients treated. The best results were achieved with the compounds of the invention.

Unlike placebo, both testosterone and the compounds of the invention proved capable of attenuating the symptoms of andropause.

Neither of the compounds tested induced pathological changes affecting the cervico-urethral district. In any event, for testosterone, as mentioned above, its use is still contraindicated in the case of disease of the prostate district as well as for the onset of troublesome adverse effects on the liver, on lipid status, on cardiovascular and prostate diseases, and on sleep and behavioural disorders.

It should be stressed that an important proportion of patients above 50 years of age suffer from diseases of the cervico-urethral district, and therefore cannot be treated with testosterone (see Exclusion criteria).

The compounds of the invention may therefore be regarded as the drugs of choice in the treatment of patients with symptoms associated with ageing, since, in addition to being more active than testosterone, they can be used in a larger number of patients.

The invention claimed is:

1. A method of treating the symptoms of disorders caused by andropause wherein said symptoms are selected from the group consisting of: reduced libido or sexual drive and reduced quality of erections, including nocturnal erections, depression of mood and fatigue comprising administering to a male subject in need of same L-carnitine, acetyl L-carnitine and propionyl L-carnitine or a pharmaceutically acceptable salt thereof, wherein the administration is according to the following schedule.:

SCHEDULE OF TREATMENT

| DAY | L-carnitine 4 g/day | L-carnitine 2 g/day | Acetyl L-carnitine 2 g/day | Propionyl L-carnitine 1 g/day | Propionyl L-carnitine 2 g/day |
|---|---|---|---|---|---|
| 1 | + | | | | |
| 2 | + | | | | |
| 3 | + | | | | |
| 4 | + | | | | |
| 5 | + | | | | |

-continued

SCHEDULE OF TREATMENT

| DAY | L-carnitine 4 g/day | L-carnitine 2 g/day | Acetyl L-carnitine 2 g/day | Propionyl L-carnitine 1 g/day | Propionyl L-carnitine 2 g/day |
|---|---|---|---|---|---|
| 6 | + | | | | |
| 7 | + | | | | |
| 8 | | + | + | | |
| 9 | | + | + | | |
| 10 | | + | + | | |
| 11 | | + | + | | |
| 12 | | + | + | | |
| 13 | | + | + | | |
| 14 | | + | + | | |
| 15 | | + | | + | |
| 16 | | + | | + | |
| 17 | | + | | + | |
| 18 | | + | | + | |
| 19 | | + | | + | |
| 20 | | + | | + | |
| 21 | | + | | + | |
| 22 | | + | | | + |
| 23 | | + | | | + |
| 24 | | + | | | + |
| 25 | | + | | | + |
| 26 | | + | | | + |
| 27 | | + | | | + |
| 28 | | + | | | + |
| 29 | | + | | | + |
| 30 | | + | | | + |
| 31 | | + | | | + |
| 1 | | + | | | + |
| 2 | | + | | | + |
| 3 | | + | | | +. |

2. The method according to claim 1, in which the andropause is caused by aging.

3. The method according to claim 1, in which the andropause is caused by chemical or surgical castration.

4. The method according to claim 1, in which the pharmaceutically acceptable salt is selected from the group consisting of: chloride, bromide, orotate, acid aspartate, acid citrate, magnesium citrate, acid phosphate, fumarate, and acid fumarate, magnesium fumarate, lactate, maleate and acid maleate, mucate, acid oxalate, pamoate, acid pamoate, acid sulphate, glucose phosphate, tartrate, acid tartrate, magnesium tartrate, 2-amino-ethane sulphonate, magnesium 2-amino-ethane sulphonate, choline tartrate and trichloroacetate.

5. The method according to claim 1, in which L-carnitine, propionyl L-carnitine and acetyl L-carnitine are in any form suitable for oral or parenteral administration.

* * * * *